(12) United States Patent
Malz, Jr. et al.

(10) Patent No.: US 6,646,127 B2
(45) Date of Patent: Nov. 11, 2003

(54) PROCESS FOR THE SYNTHESIS OF 2,2,6,6-TETRAMETHYL-4-OXOPIPERIDINE

(75) Inventors: Russell E. Malz, Jr., Naugatuck, CT (US); Young-Chan Son, Storrs, CT (US); Steven L. Suib, Storrs, CT (US)

(73) Assignees: Uniroyal Chemical Company, Inc., Middlebury, CT (US); University of Connecticut, Storrs, CT (US)

( * ) Notice: Subject to any disclaimer, the term of this patent is extended or adjusted under 35 U.S.C. 154(b) by 0 days.

(21) Appl. No.: 09/970,069

(22) Filed: Oct. 2, 2001

(65) Prior Publication Data

US 2002/0128482 A1 Sep. 12, 2002

Related U.S. Application Data

(63) Continuation-in-part of application No. 09/677,971, filed on Oct. 3, 2000.

(51) Int. Cl.⁷ .............................................. C07D 211/40
(52) U.S. Cl. ........................................ 546/216; 502/263
(58) Field of Search ........................... 546/216; 502/263

(56) References Cited

FOREIGN PATENT DOCUMENTS

EP          004104        *   9/1979

OTHER PUBLICATIONS

Tung et al. "Zeolitic aluminosilicate. I. surface ionic diffusion, dynamic field and catalytic activity with hexane on CaY" CA 68:99075 (1968).*

* cited by examiner

Primary Examiner—Ceila Chang
(74) Attorney, Agent, or Firm—Daniel Reitenbach

(57) ABSTRACT

A process for the synthesis of 2,2,6,6-tetramethyl-4-oxopiperidine is disclosed wherein the process comprises reacting in a liquid phase reaction mixture:

A) at least one acetone compound, and

B) at least one ammonia donor compound, in the presence of a catalytically effective amount of a crystalline aluminosilicate containing calcium.

22 Claims, No Drawings

PROCESS FOR THE SYNTHESIS OF 2,2,6,6-TETRAMETHYL-4-OXOPIPERIDINE

This application is a continuation in part of application Ser. No. 09/677,971 filed Oct. 3, 2000.

BACKGROUND OF THE INVENTION

1. Field of the Invention

The present invention is directed to a process for the synthesis of 2,2,6,6-tetramethyl-4-oxopiperidine, which is also known as 2,2,6,6-tetramethyl-4-piperidone and triacetonamine. For convenience, the compound will be referred to hereinafter as triacetonamine. More particularly, the present invention is directed to a process that can be carried out at room temperature for the synthesis of triacetonamine with high selectivity by reacting an acetone compound with an ammonia source in the presence of a calcium-containing catalyst.

2. Description of Related Art

Triacetonamine is a known compound that is useful as an intermediate in the preparation of drugs and 2,2,6,6-tetramethyl piperidyl and related light stabilizers for polymeric materials. Its structural formula is:

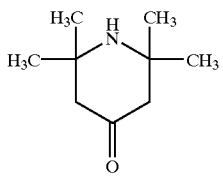

An outline of how triacetonamine is used as an intermediate in the preparation of stabilizers appears in U.S. Pat. No. 4,124,564.

Triacetonamine has been known at least since the work of Heinz, *Annalen der Chemie*, 203:336 (1880). Heinz converted acetone to phorone in about 30% yield and reacted the phorone with ammonia to yield triacetonamine in 70% yield.

Hall, *Journal of the American Chemical Society*, 79:5447 (1957) disclosed reacting acetone with ammonia in the presence of calcium chloride for nine days, thereby obtaining a yield of about 20% of triacetonamine after careful fractional distillation.

More specifically, Hall passed ammonia into a mixture of acetone and $CaCl_2$ for 30 minutes. Additional ammonia was added for 15-minute periods at intervals of 3 hours for five days. After four days of standing at room temperature, the mixture was dark and syrupy, but the calcium chloride had not liquefied. It was poured into 50% NaOH and then the upper layer was decanted from the heavy white sludge of calcium hydroxide, which was then rinsed with ether until tests with ethereal picric acid indicated the absence of amines in the extract. The combined ether layers were dried over $K_2CO_3$ and distilled to give a yellow liquid. Careful fractionation of this material through a spinning band column gave 666 g (20.0%) of triacetonamine.

Sosnovsky et al., *Synthesis* 11:735–6 (1976) describe a method for the preparation of triacetonamine in yields of 70–89% (taking into account recovered acetone) from acetone, ammonia, and calcium chloride using easily accessible laboratory equipment.

Wu et al., *Synthetic Communications* 226(19):3565–3569 (1996) describe a method for the preparation of triacetonamine in which p-nitrotoluene is used as a catalyst. Yields of triacetonamine of up to 65% are reported.

Bradbury et al., *Journal of the Chemical Society*, 1394–99 (1947) describe reactions of acetone and ammonia, alone and with a number of different catalysts, that did not give any triacetonamine. Bradbury's product, obtained in 17% yield without catalyst and in 35% to 90% yield depending on catalyst choice, was 2,2,4,4,6-pentamethyl-2,3,4,5-tetrahydropyrimidine hydrate, split to diacetonamine oxalate by the action of alcoholic oxalic acid.

U.S. Pat. No. 1,473,285 discloses the formation of a mixture of acetone amines such as diacetone amine, triacetone diamine, triacetone amine, and other products by the action of ammonia on acetone at high temperatures (100° C.) or at ordinary temperature after long standing. It is disclosed that the use of dehydrating agents such as calcium chloride greatly facilitates the reaction and also gives a product of greater value as an accelerator.

U.S. Pat. No. 3,513,170 discloses a process for the preparation of 2,2-dimethyl-4-oxo-6,6-disubstituted piperidine derivatives which comprises reacting diacetone alcohol with ammonia and a ketone derivative in the presence of a Lewis acid. This patent also discloses a process for the preparation of triacetonamine which comprises reacting 2,2,4,4,6-pentamethyl-2,3,4,5-tetrahydropyrimidine with a Lewis acid in the presence of water. The compounds are said to be useful as intermediates for the synthesis of light stabilizers for polyolefins.

U.S. Pat. No. 3,943,139 discloses the preparation of triacetonamine by heating phorone with aqueous ammonia and basic catalysts, such as lithium, sodium, calcium, or barium hydroxide, in an autoclave under pressure.

U.S. Pat. No. 3,953,459 discloses the preparation of triacetonamine from 2,2,4,4,6-pentamethyl-2,3,4,5-tetrahydropyrimidine by treatment with an acidic catalyst. Suitable catalysts are Lewis acids, protonic acids and their salts with ammonia or organic bases. The reaction may be carried out in organic solvents, preferably in acetone, by gentle heating, for example at 40° to 65° C. Yields of 95% are said to be obtainable after a reaction of several hours.

U.S. Pat. No. 3,959,295 discloses the preparation of triacetonamine from acetone and ammonia in the presence of acidic catalysts. Suitable catalysts are Lewis acids, protonic acids and their salts with ammonia or with organic bases, as for example $BF_3$, $NH_4Cl$, or $H_2SO_4$. The addition of an alcohol, such as methanol, as well as the use of a cocatalyst may promote the reaction. The process may be carried out in two steps, in the first of which the temperature is held below 35° C. In the second step, a further amount of acetone is added and the temperature is raised to about 40° to 65° C.

U.S. Pat. No. 3,959,298 discloses a process for preparing triacetonamine characterized in that acetonine is reacted with water in the presence of at least 12.5 mole % based on acetonine of an acid catalyst.

U.S. Pat. No. 3,960,875 discloses the preparation of triacetonamine from 2,2,4,4,6-pentamethyl-2,3,4,5-tetramethylpyrimidine (acetonine) by heating in the presence of acetone, diacetone alcohol or water. These reagents may be used in excess or an organic solvent is added. The preferred modification is the heating of acetonine hydrate in an excess of acetone or in an acetone-methanol mixture to about 40° to 65° C. for several hours. The use of diacetone alcohol is said to permit higher reaction temperatures leading to shorter reaction times.

U.S. Pat. No. 3,963,730 discloses a process for preparing triacetonamine, characterized in that acetonine is reacted with acetone in the presence of at least 12.5 mol % based on acetonine of an acid catalyst under anhydrous conditions.

U.S. Pat. No. 4,252,958 discloses a process for preparing triacetonamine in which a hydrazine hydrohalide salt catalyzes the reaction of an acetone compound, for example acetone or diacetone alcohol, with an ammonia donor compound, for example ammonia or acetonine.

U.S. Pat. No. 4,275,211 discloses a process for producing piperidines, including, inter alia, tiacetonamine, wherein a catalyst is used that is a strongly acid ion exchanger having a medium or large mesh size or having large macropores.

U.S. Pat. No. 4,356,308 discloses the synthesis of triacetonamine from acetone and ammonia wherein a partially halogenated or perhalogenated aliphatic or cyclic hydrocarbon is used as catalyst in an amount of from 0.01 to 5 mol %, relative to acetone.

U.S. Pat. No. 4,418,196 discloses process for preparing triacetonamine by reacting acetone and/or an acid condensate of acetone with ammonia in the presence of at least one catalyst selected from the group consisting of organotin halides, 1,3,5,2,4,6-triazatriphosphorin hexahalides and cyanuric halides.

U.S. Pat. No. 4,536,581 discloses a process for preparing triacetonamine from ammonia and acetone, wherein acetone and ammonia are reacted in a single stage for a time of 2 to 8 hours in an acetone:ammonia molar ratio of 20:1 to 4:1, at a temperature of 50° to 120° C. and at a pressure of 1 to 50 atmospheres, in the presence of 0.001–0.1 mole of acid catalysts per mole of acetone used in the reaction.

U.S. Pat. No. 4,663,459 discloses a process for the preparation of triacetonamine by reacting acetone with ammonia in the presence of a catalytically effective amount of an organic carboxylic acid halide.

U.S. Pat. No. 4,831,146 discloses a process for producing 2,2,6,6-tetraalkyl-4-oxopiperidines by the reaction of a ketone and ammonia. Ammonium hydroxide can be substituted for the ammonia. A catalytic amount of a super acid, i.e., a perfluorinated sulfonic acid polymer or perfluorinated alkyl sulfonic acid is used as the catalyst. Typically, the catalyst is supported on a porous inert solid having a pore diameter of between 50 and 600 Angstroms or higher and typically are inorganic oxides such as alumina, fluorided alumina, zirconia, silica, silica-alumina, bauxite, kieselguhr, kaolin, charcoal, porous glass, etc.

Russian Certificate of Invention No. 473,715 discloses a process for the preparation of triacetonamine by reacting acetone with ammonium carbonate in the presence of calcium chloride and subsequently isolating the end product according to known methods.

Polish Provisional Patent No. 118,992 discloses a method for synthesizing triacetonamine by reaction of acetone with ammonium chloride, which closes the ring, in the presence of calcium oxide. The reaction is conducted at a temperature around 50° C. in the presence of about 10 vol. % of water relative to the acetone used.

Hungarian Patent Disclosure No. 46,306 discloses a process for preparing triacetonamine by reacting acetone and ammonia in the presence of ammonium chloride catalyst, characterized in that the ammonia is introduced into the reaction mixture in the form of an aqueous ammonium hydroxide solution.

Japanese Patent Disclosure No.: Sho 63-[1988]-222,157 discloses a method for the synthesis of triacetonamine, characterized in that acetone and (or) an acidic condensation product of acetone and ammonia are reacted at a temperature in the range of 0–60° C. in the presence of more that 12.5 mol. %, in relation to the amounts of acetone and (or) an acidic condensation product of acetone and ammonia used, of an acid catalyst selected from among an inorganic acid, a carboxylic acid, a sulfonic acid, and a salt of these acids with ammonia or a nitrogen-containing organic base. Additional amounts of acetone and (or) the acidic condensation product of acetone are then added and the reaction is heated to complete the reaction.

W. Heintz, *Ammoniakderivate des Acetons,* Annalen 174, 133 (1874) saturated acetone with ammonia and heated at 100° C. in a sealed tube. A mixture of diacetoneamine and triacetoneamine with some other amines was obtained. Heintz correctly deduced the structure of TAA.

E. Matter, *Uber ein Neues Reaction Product aus Aceton und Ammonia,* Helv. Chim. Acta XXV 1114–1122 (1947) allowed acetone/ammonia 1:1.9 to stand 12 hours at 27–29° C. over mixture of $CaCl_2$ and $NH_4Cl$. They obtained an 82% yield of acetonin based on aetone. They demonstrated that acetonin hydrolyzed rapidly to diacetoneamine in the presence of aqueous HCl. They also were able to isolate acetonin hydrate as a discrete compound.

Keisuke Murayama et al. (Sankyo) *Stable Free Radicals I. Synthesis of 2,2,6,6-tetramethyl-4-piperidone,* Nippon Kagaku Zasshi 1969, 90(3) 296 (Japan) treated acetone with ammonia in presence of Calcium Chloride.

The disclosures of the foregoing are incorporated herein by reference in their entirety.

SUMMARY OF THE INVENTION

The present invention relates to a process that can be carried out at room temperature for the synthesis of triacetonamine with high selectivity by reacting an acetone compound with an ammonia source in a single step in the presence of a calcium-containing catalyst.

More particularly, the present invention relates to a process for the synthesis of 2,2,6,6-tetramethyl-4-oxopiperidine comprising reacting in a liquid phase reaction mixture:

A) at least one acetone compound selected from the group consisting of acetone, a condensation product of acetone with itself, and a condensation product of acetone with ammonia, and B) at least one ammonia donor compound not identical with the acetone compound selected from the group consisting of ammonia and a condensation product of acetone with ammonia, in the presence of a catalytically effective amount of a crystalline aluminosilicate containing calcium.

In a highly preferred embodiment, the present invention is directed to a process for the synthesis of 2,2,6,6-tetramethyl-4-oxopiperidine comprising reacting in a liquid phase reaction mixture in a single step at a temperature maintained in the range of from about 20° C. to about 25° C.:

A) acetone,

B) ammonium nitrate, and

C) ammonium hydroxide in the presence of a catalytically effective amount of a CaY zeolite;

wherein the molar ratio of acetone to the combination of ammonium nitrate and ammonium hydroxide is within the range of from about 1:1 to about 20:1 and the amount of CaY zeolite is within the range of from about 0.01 to about 10% by weight of the acetone.

In another preferred embodiment, the present invention is directed to a process for the synthesis of 2,2,6,6-tetramethyl-4-oxopiperidine which comprises reacting in a liquid phase reaction mixture:

A) at least one acetone compound; and

B) a combination of two ammonia compounds comprising ammonium nitrate and ammonia, in the presence of a catalytically effective amount of a crystalline aluminosilicate containing calcium, to form a reaction mixture;

wherein the ammonia is added to the reaction mixture in gaseous form, more preferably, wherein the ammonia in gaseous form is continuously added to the reaction mixture.

DESCRIPTION OF THE PREFERRED EMBODIMENT(S)

The acetone compound starting material for the synthesis of triacetonamine by the process of the present invention can be acetone; a condensation product of acetone with itself, such as diacetone alcohol, mesityl oxide, phorone, and the like; a condensation product of acetone with ammonia, such as diacetonamine, triacetonediamine, acetonine, and the like; or mixtures of the foregoing. Preferably, the acetone compound is acetone.

The ammonia donor compound starting material can be ammonia; ammonium hydroxide; a condensation product of acetone with ammonia, such as diacetonamine, triacetonediamine, acetonine, and the like; an ammonium salt of an inorganic or an organic acid, such as ammonium nitrate, ammonium chloride, ammonium bromide, ammonium iodide, ammonium sulfate, ammonium acetate, ammonium propionate, ammonium oxalate, ammonium maleate, ammonium succinate, and the like; or mixtures of the foregoing. Ammonium hydroxide and ammonium nitrate are preferred and their use in combination is most preferred. Particularly preferred is the combination of ammonia in gaseous form and ammonium nitrate.

Some combinations of starting materials that can be used according to this invention to prepare triacetonamine in the presence of a calcium-containing molecular sieve catalyst include acetone with ammonia, diacetone alcohol with ammonia; acetonine with ammonia; acetone with diacetonamine; acetone with acetonine; mesityl oxide with acetonine; diacetone alcohol with triacetonediamine; acetone with ammonia and acetonine; mesityl oxide and phorone with ammonia; diacetone alcohol and mesityl oxide with ammonia and diacetonamine; and, preferably, acetone with ammonium hydroxide and ammonium nitrate.

The relative proportions of acetone compound and ammonia donor compound can be varied over a wide range. The molar ratio of acetone compound to ammonia donor compound can, for example, be within the range of from about 1:1 to about 20:1, preferably from about 2:1 to about 10:1, most preferably from about 3:1 to about 6:1.

Catalysts to be used in the process of this invention comprise specific crystalline aluminosilicates, namely, X and Y zeolites. Crystalline aluminosilicates, or zeolites, can be in the form of agglomerates having high physical strength and attrition resistance. Methods for forming the crystalline powders into such agglomerates include the addition of an inorganic binder, generally a clay comprising a silicon dioxide and aluminum oxide, to the high purity zeolite powder in wet mixture. The blended clay zeolite mixture is extruded into cylindrical type pellets or formed into beads which are subsequently calcined in order to convert the clay to an amorphous binder of considerable mechanical strength. As binders, clays of the kaolin type, water permeable organic polymers or silica are generally used.

The zeolites have known cage structures in which the alumina and silica tetrahedra are intimately connected in an open three-dimensional network to form cage-like structures with window-like pores. The tetrahedra are cross-linked by the sharing of oxygen atoms with spaces between the tetrahedra occupied by water molecules prior to partial or total dehydration of the zeolite. The dehydration of the zeolite results in crystals interlaced with cells having molecular dimensions and thus, the crystalline aluminosilicates are often referred to as "molecular sieves" when they effect separation that is dependent essentially upon differences between the sizes of the feed molecules.

In hydrated form, crystalline aluminosilicates include type X zeolites, represented by Formula I below in terms of moles of oxides:

$(0.9\pm0.2)M_{2/n}O:Al_2O_3:(2.5\pm0.5)SiO_2:yH_2O$      (I)

where "M" is a cation having a valence of not more than 3 that balances the electrovalence of the tetrahedra and is generally referred to as an exchangeable cation, "n" represents the valence of the cation, and "y", which represents the moles of water, is a value up to about 9 depending upon the identity of "M" and the degree of hydration of the crystal. As noted from Formula I, the $SiO_2/Al_2O_3$ mole ratio is 2.5±0.5. As the X zeolite is initially prepared, the cation "M" is usually predominately sodium, that is, the major cation at the exchangeable cationic sites is sodium and the zeolite is therefore referred to as a sodium-X zeolite. Depending upon the purity of the reactants used to make the zeolite, however, cations other than sodium may be present as impurities, such as barium, lithium, copper, potassium, calcium, and mixtures thereof.

The type Y structured zeolite, in the hydrated or partially hydrated form, can be similarly represented in terms of moles of oxides as in Formula II below:

$(0.9\pm0.2)M_{2/n}O:Al_2O_3:wSiO_2:yH_2O$      (II)

where "M", "n" and "y" are the same as above and "w" is a value greater than about 3 up to about 6. The $SiO_2/Al_2O_3$ mole ratio for type Y structured zeolites can thus be from about 3 to about 6. For both zeolites, the cation "M" may be one or more of a variety of cations but, as the Y type zeolites are initially prepared, the cation "M" is also usually predominately sodium. The type Y zeolite containing predominately sodium cations at the exchangeable cationic sites is, therefore, referred to as a sodium-exchanged type-Y, or NaY, zeolite. Depending upon the purity of the reactants used to make the zeolite, however, cations other than sodium may be present as impurities, such as barium, lithium, copper, potassium, calcium, and mixtures thereof. It is highly preferred in the practice of the present invention that calcium be present in the crystalline aluminosilicate, either as an impurity or by exchange. Most preferably, the catalyst employed in the practice of the present invention is a calcium-exchanged type-Y, or CaY, zeolite.

The optimum quantity of zeolite catalyst employed in a given embodiment of the present invention can easily be determined by those skilled in the art by routine experimentation. Generally, the amount of catalyst will be within the range of from about 0.01 to about 10% by weight of the acetone compound, preferably from about 0.1 to about 5%.

A solvent or diluent is not necessary in the process of this invention, but one can be used, if desired. The solvent should be inert, and have a boiling temperature at or above the selected reaction temperature. Solvents that can be used include, for example, aliphatic hydrocarbons, such as pentane, hexane, heptane; aromatic hydrocarbons, such as benzene, toluene, xylene; chlorinated aliphatic and aromatic hydrocarbons, such as methylene chloride, trichloroethane, chloroform, carbon tetrachloride; chlorobenzene, the dichlorobenzenes and trichlorobenzenes; the chlorotoluenes and the chloroxylenes; aliphatic and cycloaliphatic alcohols, such as methanol, ethanol, isopropanol, butanol, t-butanol, 2-ethylhexanol, cyclohexanol; and aliphatic and heterocyclic ethers, such as diethyl ether, tetrahydrofuran and dioxane. Normally, the reaction will be run in the presence of excess acetone, which, in such instance, can act as a solvent as well as a reactant.

In the synthesis of triacetonamine according to the process of this invention, the presence of water is not detrimental. Some water is formed as a product of the reaction between acetone and ammonia and such water can, if desired, be removed as it forms, or allowed to accumulate and become part of the solvent system.

The reactants, catalyst, solvent and so on can be charged all at once or in several portions as the reaction proceeds. Ammonia in gaseous form can be added to the reaction mixture continuously as the reaction proceeds.

Neither reaction temperature nor reaction pressure is critical. The process of the invention will proceed at room temperature or below, as well as at elevated temperatures. Preferably, the reaction temperature is within the range from about 0° C. and the boiling point of the reaction mixture at atmospheric pressure, more preferably in the range of from about 0° C. to about 50° C., to about with ambient temperature, i.e., a range of from about 20° to about 25° C., particularly preferred. If the reaction mixture boils at 60° C. or below, the reaction temperature can, if desired, be increased to from 60° to about 110° C. by applying superatmospheric pressures of up to about 30 atmospheres, preferably up to about 5 atmospheres.

The required reaction time ranges from about 1 to about 24 hours, preferably from about 2 to about 17 hours, more preferably from about 2 to about 6 hours. Those skilled in the art will readily understand that reaction times can be shortened by elevation of reaction temperatures.

As a practical matter, in one embodiment, the reaction can be carried out in a single step in a very simple manner by simply combining the reagents and stirring the mixture. The reaction does not require either heating or cooling, unless desired, because the mixture will heat spontaneously to a temperature in the range of from about 38° to about 56° C. owing to the heat of the reaction.

At the end of the reaction, the lowest boiling components of the mixture are unreacted acetone, water, and solvent, if used; these can be stripped off and used as the solvent or diluent in subsequent preparations without separation from one another. Triacetonamine can be recovered from the reaction mixture by conventional techniques, for example, by precipitation as the hydrate by adding water; by precipitation as the hydrohalide, sulfate, or oxalate salt by adding the appropriate acid; or by distillation, suitably after adding an excess of strong alkali, such as concentrated aqueous potassium or sodium hydroxide solution.

The advantages and the important features of the present invention will be more apparent from the following examples.

EXAMPLES 1–4

In Examples 1 through 4, each reaction was run in a 100 mL 3-necked glass round bottom flask equipped with a magnetic stirrer, a thermometer, and a 25 mL dropping funnel. Each experiment was started with a 6:1 molar ratio of acetone to ammonia donor (17.4 g, 0.30 mole, of acetone and 4.0 g, 0.05 mole, of ammonia as ammonium nitrate). A quantity of 0.5 g of dry CaY zeolite was then added. Ammonium hydroxide (3.1 mL of 28–30% ammonia in water, 0.05 mole) was added over a period of 20 minutes to the mixture of ammonium nitrate, acetone, and CaY zeolite to finish with a 3:1 molar ratio of acetone to ammonia donor (ammonium hydroxide+ammonium nitrate). The temperature was maintained between about 20° C. and about 25° C.

After the reaction, residual acetone was removed by evaporation with a vacuum pump at room temperature, CaY zeolite was filtered off, and the product was washed five times with 60 mL of diethyl ether in a separatory funnel. The ether layers were separated, combined, dried with magnesium sulfate, and filtered. Residual ether was evaporated in a hood overnight. The weight of isolated product was divided by the maximum theoretical weight of triacetonamine. The results are shown in Table 1. The selectivity was determined by an area percent gas chromatography analysis of the isolated product.

TABLE 1

The Rate of Reaction with a 3:1 Ratio of Acetone to Ammonia

| Example | Time (Hours) | Yield Weight (grams) | Yield Weight (%) | Selectivity (%) |
|---|---|---|---|---|
| 1 | 2 | 0.6 | 3.8 | 99 |
| 2 | 4 | 1.8 | 11.6 | 99 |
| 3 | 6 | 2.7 | 17.4 | 99 |
| 4 | 17 | 3.4 | 21.9 | 99 |

EXAMPLES 5–8

The procedure of Examples 1–4 was repeated, except that the quantity of acetone was doubled to 34.8 grams (0.60 mole) to provide a ration of acetone to ammonia donor of 6:1. The results are shown in Table 2.

TABLE 2

The Rate of Reaction with a 6:1 Ratio of Acetone to Ammonia

| Example | Time (Hours) | Yield Weight (grams) | Yield Weight (%) | Selectivity (%) |
|---|---|---|---|---|
| 5 | 2 | 1.4 | 9.0 | 99 |
| 6 | 4 | 1.9 | 12.2 | 99 |
| 7 | 6 | 2.9 | 18.7 | 99 |
| 8 | 17 | 3.5 | 22.6 | 99 |

EXAMPLES 9–12

In Examples 9 through 12, each reaction was run in a 100 mL 3-necked glass round bottom flask equipped with a magnetic stirrer, a thermometer, and a 25 mL dropping funnel. Each Example was started with a different molar ratio of acetone to ammonia donor Example 9

58.0 g, 1.0 mole, of acetone and 4.0 g, 0.05 mole, of ammonia as ammonium nitrate (20:1 mole ratio).

Example 10

29.0 g, 0.50 mole, of acetone and 4.0 g, 0.05 mole, of ammonia as ammonium nitrate (10:1 mole ratio).

Example 11

17.4 g, 0.30 mole, of acetone and 4.0 g, 0.05 mole, of ammonia as ammonium nitrate (6:1 mole ratio).

Example 12

11.6 g, 0.20 mole, of acetone and 4.0 g, 0.05 mole, of ammonia as ammonium nitrate (4:1 mole ratio).

A quantity of 0.5 g of dry CaY zeolite was then added to the reactants of each Example.

Ammonium hydroxide (3.1 mL of 28–30% ammonia in water, 0.05 mole) was added over a period of 20 minutes to each of the mixtures of ammonium nitrate, acetone, and CaY zeolite to finish with molar ratios of acetone to ammonia donor (ammonium hydroxide+ammonium nitrate) of 10:1, 5:1, 3:1 and 2:1 in Examples 9, 10, 11, and 12, respectively. In each Example, the temperature was maintained between about 20° C. and about 25° C. for four hours.

After each reaction, residual acetone was removed by evaporation with a vacuum pump at room temperature, CaY zeolite was filtered off, and the product was washed five times with 60 mL of diethyl ether in a separatory funnel. In each case, the ether layers were separated, combined, dried with magnesium sulfate, and filtered and residual ether was evaporated in a hood overnight. Selectivities were determined by area percent gas chromatography analyses of the isolated products. The results are shown in Table 3, wherein the side products were identified by GC-MS and N.D. stands for "None Detected", D=diacetone alcohol, P=phorone, A=acetonine, and U=unknown.

TABLE 3

Effect of the Ratio of Acetone to Ammonia Donor

| Example | Ratio of Acetone to Ammonia | Weight (grams) | Yield (%) | Selectivity | Side Products |
|---|---|---|---|---|---|
| 9 | 10:1 | 2.4 | 15.4 | 99% | N.D. |
| 10 | 5:1 | 1.9 | 12.3 | 99% | N.D. |
| 11 | 3:1 | 1.8 | 11.6 | 99% | N.D. |
| 12 | 2:1 | 0.9 | 5.8 | 55% | D, P, A, U |

EXAMPLES 13–22

In Examples 13 through 22, each reaction was run in a 100 mL 3-necked glass round bottom flask equipped with a magnetic stirrer, a thermometer, and a 25 mL dropping funnel. Each experiment was started with a 6:1 molar ratio of acetone to ammonia donor (17.4 g, 0.30 mole, of acetone and 4.0 g, 0.05 mole, of ammonia as ammonium nitrate). A quantity of 0.5 g of dry CaY zeolite was then added in Example 21; in Examples 13–20 and 22, 0.0045 mole of the catalysts indicated in Table 4 were employed. Ammonium hydroxide (3.1 mL of 28–30% ammonia in water, 0.05 mole) was added over a period of 20 minutes to the mixture of ammonium nitrate, acetone, and catalyst to finish with a 3:1 molar ratio of acetone to ammonia donor (ammonium hydroxide+ammonium nitrate). The temperature was maintained between about 20° C. and about 25° C. for four hours.

After the reactions, residual acetone was removed by evaporation with a vacuum pump at room temperature and each product was washed five times with 60 mL of diethyl either in a separatory funnel. In each case, the ether layers were separated, combined, dried with magnesium sulfate, and filtered. Residual ether was evaporated in a hood overnight. Selectivities were determined by area percent gas chromatography analyses of the isolated products. The results are shown in Table 4, wherein the side products were identified by GC-MS and N.D. stands for "None Detected", D=diacetone alcohol, P=phorone, A=acetonine, U=unknown, and N.R.="No Reaction".

TABLE 4

The Effect of Various Catalysts

| Example | Catalyst | Weight (grams) | Yield Weight (%) | Selectivity | Side Products |
|---|---|---|---|---|---|
| 13 | Na$_2$SiO$_3$ | 1.4 | 9.0 | 85% | A, U |
| 14 | Zn(OAc)$_2$ | 0.4 | 2.6 | 99% | N.D. |
| 15 | Mn(OAc)$_2$·4H$_2$O | N.R. | — | — | — |
| 16 | BaO | 1.1 | 7.1 | 98% | A, U |
| 17 | Sr(NO$_3$) | 2.4 | 15.5 | 84% | A, D, U |
| 18 | Ca(OAc)$_2$ | 2.2 | 14.2 | 91% | A |
| 19 | Mg(NO$_3$)$_2$ | N.R. | — | — | — |
| 20 | Ca(NO$_3$)$_2$ | 1.8 | 11.6 | 91% | A, U |
| 21 | CaY | 1.8 | 11.6 | 99% | N.D. |
| 22 | CaCl$_2$ | 2.0 | 12.9 | 94% | A |

EXAMPLES 23–25

In Examples 23 through 25, each reaction was run in a 100 mL 3-necked glass round bottom flask equipped with a magnetic stirrer, a thermometer, and a 25 mL dropping funnel. Each experiment was started with a 6:1 molar ratio of acetone to ammonia donor (17.4 g, 0.30 mole, of acetone and 0.05 mole of ammonia donor as ammonium nitrate (4.0 g), or ammonium sulfate (6.6 g), or ammonium chloride (2.67 g)). A quantity of 0.5 g of dry CaY zeolite was then added. Ammonium hydroxide (3.1 mL of 28–30% ammonia in water, 0.05 mole) was added over a period of 20 minutes to the mixture of ammonium donor, acetone, and CaY zeolite to finish with a 3:1 molar ratio of acetone to total ammonia donor (ammonium hydroxide+ammonium nitrate, sulfate, or chloride). The temperature was maintained between about 20° C. and about 25° C. for 4 hours in Example 23 and for 24 hours in each of Examples 24 and 25.

After the reactions, residual acetone was removed by evaporation with a vacuum pump at room temperature, CaY was filtered off, and each product was washed five times with 60 mL of diethyl ether in a separatory funnel. In each case, the ether layers were separated, combined, dried with magnesium sulfate, and filtered. Residual ether was evaporated in a hood overnight. Selectivities were determined by area percent gas chromatography analyses of the isolated products. The results are shown in Table 5, wherein the side products were identified by GC-MS and N.D. stands for "None Detected", D=diacetone alcohol, P=phorone, A=acetonine, and U=unknown.

TABLE 5

The Effect of Ammonia Source

| Example | Ammonia Source | Weight (grams) | Yield Weight (%) | Selectivity | Side Products |
|---|---|---|---|---|---|
| 23 | NH$_4$NO$_3$ | 1.8 | 11.6 | 99% | N.D. |
| 24 | (NH$_4$)$_2$SO$_4$ | 0.5 | 3.2 | 25% | D, P, A, U |
| 25 | NH$_4$Cl | 0.6 | 3.9 | 40% | D, P, A, U |

EXAMPLES 26–29

In Examples 26 through 29, each reaction was run in a 100 mL 3-necked glass round bottom flask equipped with a magnetic stirrer, a thermometer, and a 25 mL dropping funnel. Each experiment was started with a 6:1 molar ratio of acetone to ammonia donor (17.4 g, 0.30 mole, of acetone and 4.0 g, 0.05 mole, of ammonia as ammonium nitrate). A quantity of 0.5 g (0.0045 mole) of $CaCl_2$ was then added. Ammonium hydroxide (3.1 mL of 28–30% ammonia in water, 0.05 mole) was added over a period of 20 minutes to the mixture of ammonium nitrate, acetone, and CaY zeolite to finish with a 3:1 molar ratio of acetone to ammonia donor (ammonium hydroxide+ammonium nitrate). The temperature was maintained between about 20° C. and about 25° C.

After the reaction, residual acetone was removed by evaporation with a vacuum pump at room temperature and the product was washed five times with 60 mL of diethyl ether in a separatory funnel. The ether layers were separated, combined, dried with magnesium sulfate, and filtered. Residual ether was evaporated in a hood overnight. Selectivities were determined by area percent gas chromatography analyses of the isolated products. The results are shown in Table 6, wherein the side products were identified by GC-MS and D=diacetone alcohol, P=phorone, A=acetonine, and U=unknown.

TABLE 6

The Effect of Time When $CaCl_2$ Was Used as a Catalyst

| Example | Time (Hours) | Weight (grams) | Weight (%) | Selectivity | Side Products |
|---|---|---|---|---|---|
| 26 | 15 | 3.2 | 20.6 | 92% | D, P, A, U |
| 27 | 6 | 2.7 | 17.4 | 93% | A |
| 28 | 4 | 2.3 | 14.8 | 93% | A |
| 29 | 2 | 1.8 | 11.6 | 90% | D, P, A |

EXAMPLES 30–32

In Examples 30–32, each reaction was run in a 100 mL 3-necked glass round bottom flask equipped with a magnetic stirrer, a thermometer, and a 25 mL dropping funnel. Each experiment was started with a 6:1 molar ratio of acetone to ammonia donor (17.4 g, 0.30 mole, of acetone and 4.0 g, 0.05 mole, of ammonia as ammonium nitrate). A quantity of 0.5 g of dry CaY zeolite was then added, followed by, in Examples 31 and 32, 1.0 g of desiccant. The flask was sealed, agitation was begun, and a total of 0.05 moles of ammonia was added to the flask by flowing 0.026 moles/hr of ammonia in gaseous form into the flask over a two-hour period. The final ratio of acetone to ammonia donor (ammonia+ammonium nitrate) was 3:1. The temperature was maintained between about 20° C. and about 25° C.

After the reaction, CaY zeolite was filtered off, residual acetone was removed by evaporation with a vacuum pump at room temperature, and the product was washed five times with 60 mL of diethyl ether in a separatory funnel. The ether layers were separated, combined, dried with magnesium sulfate, and filtered. Residual ether was evaporated in a hood overnight. The weight of isolated product was divided by the maximum theoretical weight of triacetonamine. The results are shown in Table 7 below. The selectivity was determined by an area percent gas chromatography analysis of the isolated product.

EXAMPLES 33 AND 34

The same procedure as described above for Examples 30–32 was conducted except that after the 0.05 moles of ammonia was added, the flask was unsealed and, in Example 33, an additional 8.7 g (0.15 mole) of acetone was added to the flask, and, in Example 34, an additional 17.4 g (0.30 mole) of acetone was added to the flask. After the additional acetone was added to the flask, the flask was resealed and the reaction was continued for fifteen (15) hours. The final ratio of acetone to ammonia donor (ammonia+ammonium nitrate) in Example 33 was 4.5:1 and in Example 34 was 6:1. The results are shown in Table 7 below.

TABLE 7

| Example | Desiccant Type | Desiccant g. | YIELD g. | YIELD Mole % | Selectivity |
|---|---|---|---|---|---|
| 30 | (None) | — | 5.9 | 38.0 | 98% |
| 31 | $Na_2SO_4$ | 1.0 | 6.3 | 40.6 | 98% |
| 32 | $MgSO_4$ | 1.0 | 6.6 | 42.6 | 98% |
| 33 | (None) | — | 7.2 | 46.5 | 98% |
| 34 | $MgSO_4$ | 1.0 | 8.5 | 54.8 | 98% |

In view of the many changes and modifications that can be made without departing from principles underlying the invention, reference should be made to the appended claims for an understanding of the scope of the protection to be afforded the invention.

What is claimed is:

1. A process for the synthesis of 2,2,6,6-tetramethyl-4-oxopiperidine comprising reacting in a liquid phase reaction mixture:
   A) at least one acetone compound, and
   B) at least one ammonia donor which is a compound selected from an ammonium salt of an inorganic acid, an ammonium salt of an organic acid and mixtures thereof, in the presence of a catalytically effective amount of a crystalline aluminosilicate containing calcium.

2. The process of claim 1 further comprising the step of recovering 2,2,6,6-tetramethyl-4-oxopiperidine from the reaction mixture.

3. The process of claim 1 wherein the acetone compound is selected from the group consisting of acetone, a condensation product of acetone with itself, and a condensation product of acetone with ammonia, and mixtures thereof.

4. The process of claim 3 wherein the acetone compound is acetone.

5. The process of claim 1 wherein the ammonia donor further comprises a condensation product of acetone with ammonia.

6. The process of claim 1 wherein the ammonia donor is an ammonium salt of an inorganic acid.

7. The process of claim 6 wherein the salt is ammonium nitrate.

8. The process of claim 1 wherein the ammonia donor further comprises ammonium hydroxide.

9. The process of claim 1 wherein the ammonia donor further comprises ammonia.

10. The process of claim 9 wherein the ammonia is in gaseous form and is added continuously to the reaction mixture.

11. The process of claim 1 wherein the ammonia donor is ammonium nitrate further comprising ammonia.

12. The process of claim 11 wherein the ammonia is in gaseous form and is continuously added to the reaction mixture.

13. The process of claim 1 wherein the ammonia donor is ammonium nitrate further comprising ammonium hydroxide.

14. The process of claim 1 wherein the crystalline aluminosilicate containing calcium is a calcium-containing zeolite.

15. The process of claim 14 wherein the calcium-containing zeolite is a CaY zeolite.

16. The process of claim 1 wherein the reaction is carried out in a single step.

17. The process of claim 1 wherein the molar ratio of acetone compound to ammonia donor compound is within the range of from about 1:1 to about 20:1.

18. The process of claim 1 wherein the amount of crystalline aluminosilicate is within the range of from about 0.01 to about 10% by weight of the acetone compound.

19. The process of claim 1 wherein the reaction is carried out at ambient temperature.

20. The process of claim 1 wherein the temperature of the reaction is maintained in the range of from about 0° C. to about 50° C.

21. A process for the synthesis of 2,2,6,6-tetramethyl-4-oxopiperidine comprising reacting in a liquid phase reaction mixture in a single step at a temperature maintained in the range of from about 20° to about 25° C.:

A) acetone,

B) ammonium nitrate, and

C) ammonium hydroxide in the presence of a catalytically effective amount of a CaY zeolite;

wherein the molar ratio of acetone to the combination of ammonium nitrate and ammonium hydroxide is within the range of from about 1:1 to about 20:1 and the amount of CaY zeolite is within the range of from about 0.01 to about 10% by weight of the acetone.

22. A process for the synthesis of 2,2,6,6-tetramethyl-4-oxopiperidine comprising reacting in a liquid phase reaction mixture at a temperature maintained in the range of from about 20° C. to about 25° C.:

A) acetone,

B) ammonium nitrate, and

C) ammonia, in the presence of a catalytically effective amount of a CaY zeolite;

wherein the molar ratio of acetone to the combination of ammonium nitrate and ammonia is within the range of from about 1:1 to about 20:1 and the amount of CaY zeolite is within the range of from about 0.01 to about 10% by weight of the acetone, and wherein the ammonia is in gaseous form and is continuously added to reaction mixture.

* * * * *